United States Patent
Wang et al.

(10) Patent No.: US 12,012,595 B2
(45) Date of Patent: Jun. 18, 2024

(54) PEPTIDE LIBRARY CONSTRUCTING METHOD AND RELATED VECTORS

(71) Applicant: Hunan Zonsen Peplib Biotech Co., Ltd, Hunan (CN)

(72) Inventors: Zhuying Wang, Monmouth Junction, NJ (US); Xiangqun Li, Lutherville, MD (US)

(73) Assignee: HUNAN ZONSEN PEPLIB BIOTECH CO., LTD, Hunan (CN)

( * ) Notice: Subject to any disclaimer, the term of this patent is extended or adjusted under 35 U.S.C. 154(b) by 1003 days.

(21) Appl. No.: 15/580,961

(22) PCT Filed: Jul. 3, 2015

(86) PCT No.: PCT/CN2015/083260
§ 371 (c)(1),
(2) Date: Dec. 8, 2017

(87) PCT Pub. No.: WO2017/004745
PCT Pub. Date: Jan. 12, 2017

(65) Prior Publication Data
US 2018/0179519 A1 Jun. 28, 2018

(51) Int. Cl.
*C12N 15/10* (2006.01)
*C40B 40/10* (2006.01)
*C40B 50/06* (2006.01)

(52) U.S. Cl.
CPC .......... *C12N 15/1093* (2013.01); *C40B 40/10* (2013.01); *C40B 50/06* (2013.01)

(58) Field of Classification Search
CPC ................................................ C12N 15/1093
See application file for complete search history.

(56) References Cited

U.S. PATENT DOCUMENTS 7,105,341 B2 * 9/2006 Kinsella .................... 435/320.1
2013/0029879 A1 1/2013 Shetty et al.

FOREIGN PATENT DOCUMENTS

WO 03040391 5/2003
WO 2013063366 5/2013

OTHER PUBLICATIONS

UniProtKB—P27986 (P85A_HUMAN) Phosphatidylinositol 3-kinase regulatory subunit alpha at https://www.uniprot.org/uniprot/P27986, downloaded Aug. 4, 2021 (Year: 2021).*
Written Opinion and International Search Report for International Application No. PCT/CN2015/083260 dated Mar. 30, 2016.

* cited by examiner

*Primary Examiner* — Kaijiang Zhang
(74) *Attorney, Agent, or Firm* — RANKIN, HILL & CLARK LLP

(57) ABSTRACT

An improved peptide library preparation method is described for constructing complete peptide libraries such as a complete tripeptide library, tetrapeptide library, pentapeptide library, hexapeptide library, heptapeptide library, or a complete octapeptide library, etc. The method includes constructing an expression vector for the expression of tagged peptides. Each tagged peptide contains an array of peptides of different sizes, and the number of peptides in a complete peptide library can be dramatically reduced relative to conventional chemical peptide synthesis. Furthermore, the libraries can be readily reproduced. The improved peptide library preparation method can particularly be used, for example, to construct a complete pentapeptide library. Other related methods and related expression vectors are also described.

9 Claims, 3 Drawing Sheets
Specification includes a Sequence Listing.

PEPTIDE LIBRARY CONSTRUCTING METHOD AND RELATED VECTORS

FIELD OF THE INVENTION

The invention relates to a method for constructing complete peptide libraries such as a complete tripeptide library, tetrapeptide library, pentapeptide library, hexapeptide library, heptapeptide library, or a complete octapeptide library, etc. The method includes constructing an expression vector for the expression of the tagged peptides. Each tagged peptide contains an array of peptides of different sizes, and the number of peptides in a complete peptide library can be dramatically reduced relative to conventional chemical peptide synthesis. Furthermore, the libraries can be easily reproduced. The improved peptide library preparation method can particularly be used, for example, to construct a complete pentapeptide library.

BACKGROUND OF THE INVENTION

Peptide libraries, which contains a great number of peptides that have a systematic combination of amino acids, are widely applied as a powerful tool for screening large numbers of peptides in the search for critical bioactive peptides in biological research, protein related study and drug development. Peptides with low molecular weight have been known to be less allergenic and the diverse physiological roles of peptides make them suitable candidates for the development of therapeutic agents (Host A, Halken S. Hypoallergenic formulas—when, to whom and how long: after more than 15 years we know the right indication!. Allergy 2004 August; 59(Suppl. 78):45-52; Lax R. The future of peptide development in the pharmaceutical industry. Phar Manufacturing: Int Pept Rev 2010; Agyei D, Danquah M K. Industrialscale manufacturing of pharmaceuticalgrade bioactive peptides. Biotechnol Adv 2011 May-June; 29(3):272-7.). Bioactive peptides are therefore suitable candidates for a new era of pharmaceutical products, especially with the heightened concerns of side effects of small molecule drugs and the increased attention to fresher and 'greener' foods and nutraceuticals possessing health-preventing or health-promoting properties (Danquah M K, Agyei D. Pharmaceutical applications of bioactive peptides. OA Biotechnology 2012 Dec. 29; 1(2):5).

Many kinds of bioactive peptides have been found, which include antimicrobial, anticancer, antioxidative, antihypertensive, antithrombotic, opioid, antiviral, cytomodulatory and immunomodulatory peptides, etc. (Sharma S, Singh R, Rana S. Bioactive peptide: A Review. Int. J. Bio$_{AUTOMATION}$ 2011 15(4):223-250; Danquah M K, Agyei D. Pharmaceutical applications of bioactive peptides. OA Biotechnology 2012 Dec. 29; 1(2):5). Therefore, peptide drug development is one of the most promising fields in the development of the new drugs.

Since peptide library provides a powerful tool for drug development, protein-protein interactions, and other biochemical as well as pharmaceutical applications, several methods have been developed to construct peptide libraries. These peptide library construction methods fall into two categories: by using synthetic chemistry tools and by biotechnological approaches. Introduced in 1985 by George P. Smith, the phage display technology allows the screening of a vast amount of different peptides (Smith, G P. Filamentous fusion phage: novel expression vectors that display cloned antigens on the virion surface. Science 1985, 228, 1315-1317). It was found that the success of phage derived peptides essentially depends on the quality of the library screened (Lindner T, Kolmar H, Haberkorn U and Mier W. DNA Libraries for the Construction of Phage Libraries: Statistical and Structural Requirements and Synthetic Methods. Molecules 2011, 16, 1625-1641), however, there is no practical method to monitor or guarantee the quality of the phage display library. Indeed, until now only few of the peptides selected by phage display have entered clinical applications (Lindner T, Kolmar H, Haberkorn U and Mier W. DNA Libraries for the Construction of Phage Libraries: Statistical and Structural Requirements and Synthetic Methods. Molecules 2011, 16, 1625-1641).

Based on the solid phase synthesis developed by Merrifield, the combinatorial "split-mix synthesis" method was developed for peptide library construction (Á. Furka, F. Sebestyen, M. Asgedom, G Dibo, General method for rapid synthesis of multicomponent peptide mixtures. Int. J. Peptide Protein Res., 1991, 37, 487-493). Theoretically a huge number of peptides can be synthesized in this way to make a large library, however in practice, the number and quantity of the peptides synthesized in this way is limited duo to the high cost and low production yields of synthesizing the library.

A peptide library can also be constructed by synthesizing a large number of distinct peptides. Since there is no good way to predict which peptide will be a good drug candidate, it is desired to construct a complete peptide library, which contains all possible combinations of the amino acids, for high chance of finding good drug candidates during peptide screening. There are 20 natural occurring amino acids, 8,000 tripeptides need to be synthesized to construct a complete tripeptide library. In a similar way, 160,000 tetrapeptides need to be synthesized to construct a complete tetrapeptide library, 3,200,000 pentapeptides need to be synthesized to construct a complete pentapeptide library, and 64,000,000 hexapeptides need to be synthesized to construct a complete hexapeptide library. Again, due to the high cost and low production yields to synthesize the large number of peptides, a complete tetrapeptide library, which should contain 160,000 tetrapeptides, is even not currently available in the market, not to mention a complete pentapeptide or hexapeptide library.

Thus, there is still a need for a highly productive process for constructing peptide libraries with large capacities. Embodiments of the present invention relate to such a process for constructing peptide libraries with large capacities.

BRIEF SUMMARY OF THE INVENTION

It is an object of this invention to provide novel methods for constructing complete peptide libraries that express and display a large number of diverse sizes of peptides, polypeptides or proteins. A peptide of up to 200 amino acids will be designed in such a way that: (i) the peptide won't form significant tertiary structure as predicted by protein structure prediction tools available; (ii) the peptide will contain as few as possible short peptide repeats thus to increase the capacity of the peptide library. The peptide will be expressed as a C-terminal tail of a tag protein such as GST, SUMO, CBD, etc. The tag will be expressed first and then correctly folded, the peptide tail will be expressed later as a free-moving tail. The peptide will be displayed at the C-terminal of the tag protein, so called "protein display", the tag will facilitate the expression and purification of the peptide. The peptide library constructed in this way is called "protein display" peptide library.

It is another object of this invention to provide a method for displaying a large number of peptides from a single expressed peptide, a method to increase the library capacity significantly. For example, with reasonable designing, an expressed peptide of 50 amino acids can actually contain 47 distinct consecutive tetrapeptide, 46 distinct consecutive pentapeptide, 45 distinct consecutive hexapeptide, 44 distinct consecutive heptapeptide, . . . , 3 distinct consecutive 48-mer peptides, 2 distinct consecutive 49-mer peptides and 1 50-mer peptide, which constitutes 408 peptides with sizes ranging from 4 to 50 amino acids.

It is yet another object of this invention to provide a method for constructing a complete peptide library with a significantly reduced peptide number. For example, with reasonable designing, an expressed peptide of 50 amino acids can actually contain 47 distinct consecutive tetrapeptide, 3,405 expressed 50-mer peptides can constitute a complete tetrapeptide library, however, 160,000 synthetic tetrapeptide are needed to construct a complete tetrapeptide library. 3,405 synthetic 50-mer peptides can also constitute a complete tetrapeptide library, but the cost will be too high due to the low production yields to synthesize so many long (50-mer) peptides. However, there is no problem to express a tagged peptide whether the peptide is long (50-mer) or short.

It is yet another object of this invention to provide a method for constructing a complete pentapeptide library. With reasonable designing, an expressed peptide of 50 amino acids can actually contain 46 distinct consecutive pentapeptide, 69,566 expressed 50-mer peptides instead of 3,200,000 synthetic pentapeptides are only needed to construct a complete pentapeptide library by this protein display method.

It is yet another object of this invention to provide a method for constructing an incomplete peptide library with a significantly reduced peptide number. For longer peptides such as octapeptide, decapeptide, or even longer peptide such as 15-mer or 20-mer peptide, the complete libraries will contain huge numbers of all possible peptides, which are $2.56 \times 10^{10}$, $1.024 \times 10^{13}$, $3.277 \times 10^{19}$, $1.049 \times 10^{26}$, respectively. Therefore, it is not practical to chemically synthesize so many peptides to make a complete peptide library. However, it may not be always necessary to construct a complete library since some peptides will share high sequence similarity. By rational designing, the number of peptides to construct an efficient peptide library can be greatly reduced. This method of the invention will further reduce the peptide number in a peptide library, thus to make the construction of an efficient peptide library practical.

It is a further object of this invention to provide an alternative method for constructing a complete peptide library. The DNA sequence of each peptide will be cloned into an expression vector for the expression and purification of the tagged peptide. The vector can be stored and the peptide can be expressed or reproduced from the vector readily at any time. Unlike peptide synthesis, each peptide needs to be resynthesized from scratch. Another advantage for this method is that the tagged peptides of different sizes can be expressed and purified with the similar easiness, however, longer peptides will need much more effort than similar short peptides during chemical synthesis.

It is an object of this invention to provide a method for constructing expression vectors for the expression and purification of the tagged peptides for the peptide library construction.

Additional objects of the invention are reflected in the original claims. The details of embodiments of the disclosure are set forth in the accompanying drawings and the description below. Other features, objects, and advantages will be apparent from the description and drawings, and from the claims.

BRIEF DESCRIPTION OF THE SEVERAL VIEWS OF THE DRAWINGS

The foregoing brief summary, as well as the following detailed description of the invention, will be better understood when read in conjunction with the appended drawings. For the purpose of illustrating the invention, there are shown in the drawings embodiments which are presently preferred. It should be understood, however, that the invention is not limited by the drawings presented.

In the drawings.

DETAILED DESCRIPTION OF THE INVENTION

Unless defined otherwise, all technical and scientific terms used herein have the same meaning as is commonly understood by one of skill in the art to which this invention belongs. All publications and patents referred to herein are incorporated by reference.

Embodiments of the present invention relate to methods and vectors useful for constructing a peptide library. In one aspect, the invention relates to a significant improvement of the construction of a peptide library by conventional chemical synthesis. For example, the present invention provides an improved peptide library construction method whereby the peptides are expressed and purified readily and the number of peptides to form a library is significantly reduced.

According to embodiments of the present invention, the amino acid sequences of peptides are rationally designed so that each tagged peptide can contain an array of distinct peptides of different sizes, thus to increase the capacity of the library. Depending on the size of the tagged peptide, each peptide can contain 20, 30, 50, or even 100 of distinct peptides of a specific size. Therefore, methods according to embodiments of the present invention greatly reduce the peptide number in a peptide library, thus the construction and screening of a peptide library will be performed at significantly reduced costs.

As used herein, the terms a "peptide", a "library", a "tag", a "protein", a "vector", "capacity", "complete" and an "array" are to be taken in their broadest context.

Figure 1:
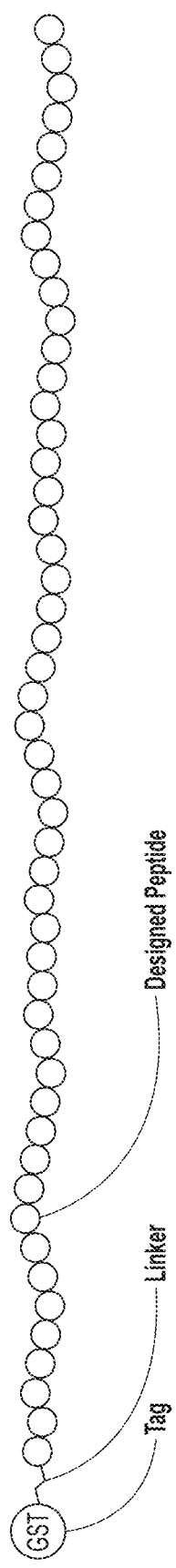
FIG. 1 schematically illustrates the protein display technology according to an embodiment of the invention.

In one general aspect, the present invention relates to a method of constructing complete peptide libraries with reduced peptide numbers as compared to the conventional peptide synthesis method. For example, as illustrated in FIG. 1, a relatively long peptide is readily expressed and purified at the C-terminal of a protein tag, or the peptide is displayed at the end of a protein, namely "protein display". Compared with protein expression, chemical synthesis of relatively long peptides is neither efficient nor cost effective. For example, a 50-mer peptide will take several days for chemical synthesis, while the similar peptide can be readily expressed in a bacteria host overnight. The overall yield of chemically synthesized 50-mer peptide will be low, while the similar peptide can be readily expressed in an expression host at any scale. In contrast, an embodiment of the present invention provides a method whereby a complete peptide library can be constructed with significantly reduced peptide number, these peptides can be readily expressed and purified, and these peptides can be readily reproduced at any time. The method according to the embodiment of the present invention has greatly cut down the time and the cost required for peptide library construction.

Embodiments of the invention relate to protein tags useful in displaying peptides. One of the protein tags is GST (glutathione S-transferase), which is commonly used to purify a target protein fused with GST. GST can help the expression of the target protein or peptide.

In one embodiment of the invention, the protein tag comprises one of the tags selected from, but not limited to, for example, GST, Trx, SUMO, CBD, FLAG; HA, AviTag, His Tag, Myc-Tag, SBP, Strep-Tag, Fc-Tag, Halo-Tag, V5, VSV, MBP, etc.

In one embodiment of the invention, the protein tag comprises a combination of the tags selected from, but not limited to, for example, GST, Trx, SUMO, CBD, FLAG; HA, AviTag, His Tag, Myc-Tag, SBP, Strep-Tag, Fc-Tag, Halo-Tag, V5, VSV, MBP, etc.

In yet a further embodiment of the invention, additional tags can be added at the C-terminal of the peptide or even in the middle of the peptide to facilitate the expression and purification of the peptide. The protein tags can be selected from, but not limited to, GST, Trx, SUMO, CBD, FLAG; HA, AviTag, His Tag, Myc-Tag, SBP, Strep-Tag, Fc-Tag, Halo-Tag, V5, VSV, MBP, etc.

A short peptide linker of a few amino acids or more can be added between the tag and the peptide to increase the accessibility of the peptide.

A protease recognition sequence can also be added between the tag and the peptide so that the peptide can be cleaved from the tag using a protease if necessary. It is apparent to those skilled in the art that the present invention includes modifications to the above-mentioned embodiments to further improve the library construction. These modifications include, but are not are limited to, adding one or multiple peptide sequences to the above embodiment. For example, one can add a few Cys amino acids in the peptide to form disulfide bond to strain the peptide structure.

A variety of methods can be used to design the peptide sequences to prepare an efficient peptide library in view of the present disclosure. For example, to facilitate the soluble expression of the tagged peptide, peptide sequences containing long stretches of hydrophobic amino acids should be avoided.

It is apparent to those skilled in the art that the peptide can be designed in such a way that it won't form significant tertiary structure as can be predicted by protein structure prediction tools available.

It is also apparent to those skilled in the art that the peptide can be designed in such a way that the peptide can contain as many as possible distinct short peptides thus to increase the capacity of the peptide library.

Figure 2:
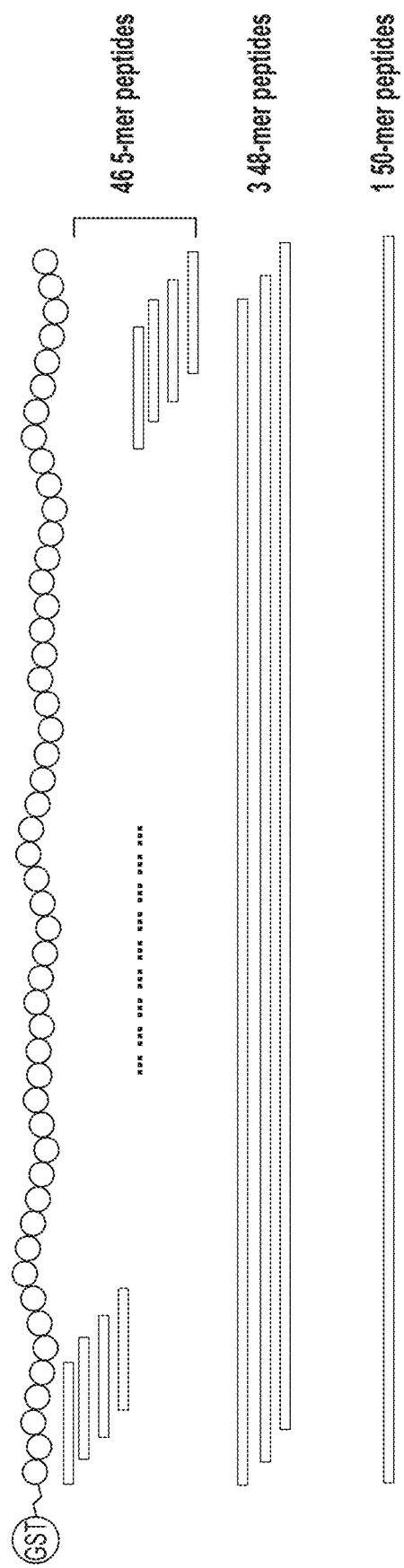
FIG. 2 schematically illustrates the high capacity of tagged peptides expressed in an expression host according to an embodiment of the invention.

According to embodiments illustrated in FIG. 2, an expressed peptide of 50 amino acids can actually contain 47 distinct consecutive tetrapeptide, 46 distinct consecutive pentapeptide, 45 distinct consecutive hexapeptide, 44 distinct consecutive heptapeptide, . . . , 3 distinct consecutive 48-mer peptides, 2 distinct consecutive 49-mer peptides and 1 50-mer peptide, which constitutes 408 peptides with sizes ranging from 4 to 50 amino acids.

In the above-mentioned embodiments, those skilled in the art will know that the tagged peptide can even contain up to 200 or more amino acids, although the optimal size will be between 30 to 100. Longer peptides will have higher chances to form tertiary structures in which some peptide sequences will not be exposed for screening.

In the above-mentioned embodiments, those skilled in the art will know that instead of synthesizing 160,000 tetrapeptides chemically, 3,405 expressed 50-mer peptides can constitute a complete tetrapeptide library.

In the above-mentioned embodiments, those skilled in the art will know that instead of synthesizing 3,200,000 pentapeptides chemically, 69,566 expressed 50-mer peptides can constitute a complete pentapeptide library.

In the above-mentioned embodiments, those skilled in the art will know that some peptides in a peptide library will share high sequence similarity and the number of peptides to construct an efficient peptide library can be greatly reduced by rational designing. Therefore, a smaller number than 3,405 of expressed 50-mer peptides can constitute an efficient tetrapeptide library. Similarly, a smaller number than 69,566 of expressed 50-mer peptides can constitute an efficient pentapeptide library.

In the above-mentioned embodiments, those skilled in the art will know that the tagged peptide can contain more than 50 amino acids, thus to further reduce the number of the expressed tagged peptides. Therefore, an even smaller number of expressed peptides can constitute an efficient tetrapeptide or pentapeptide library.

In the above-mentioned embodiments, those skilled in the art will know that some peptides in a peptide library will share high sequence similarity and structure similarity, and the number of peptides to construct an efficient peptide library can be further reduced by rational designing. Therefore, a practical number of expressed tagged peptides can constitute an efficient polypeptide library, such as an octapeptide library, a decapeptide library, or even longer peptide libraries, such as 15-mer peptide library, 20-mer peptide library or even 30-mer peptide library.

In a preferred embodiment, 69,566 expressed GST-tagged 50-mer peptides can be designed, cloned into an expression vector, expressed and purified to constitute a complete pentapeptide library.

In the above-mentioned embodiments, those skilled in the art will know that other tag or tags can also be used instead of GST, the tags can be selected from, but not limited to, Trx, SUMO, CBD, FLAG HA, AviTag, His Tag, Myc-Tag, SBP, Strep-Tag, Fc-Tag, Halo-Tag, V5, VSV, MBP, etc.

In the above-mentioned embodiments, those skilled in the art will know that the tagged peptide can contain more than or less than 50 amino acids, thus to further reduce or increase the number of the expressed tagged peptides to constitute a complete peptide library.

Figure 3:
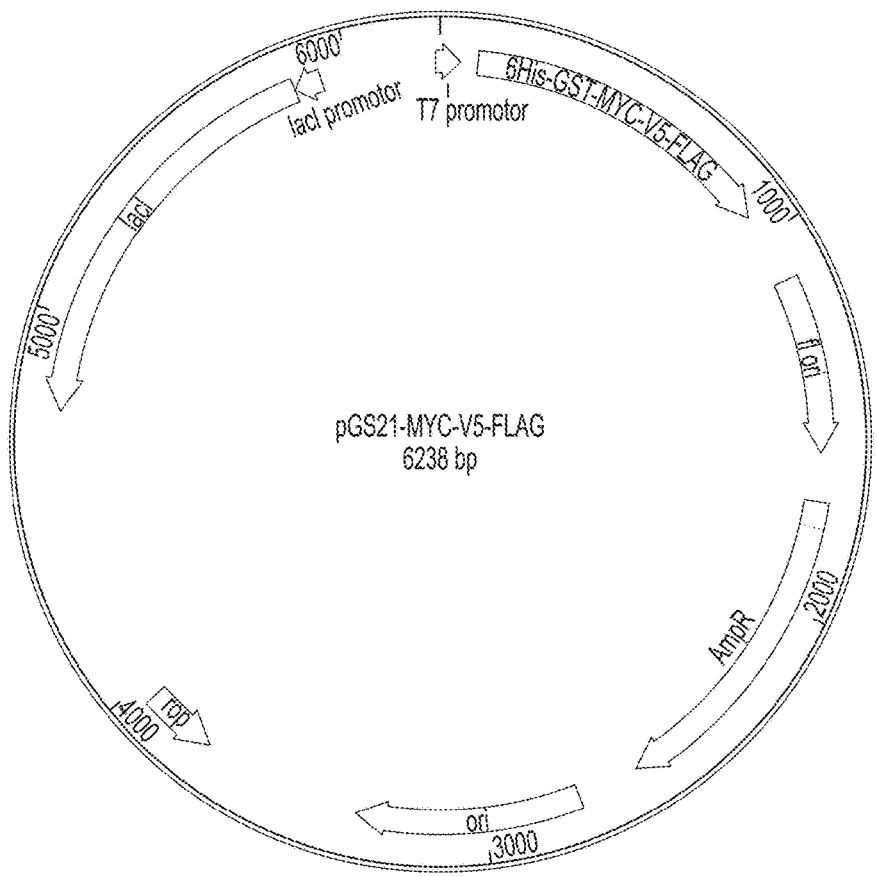
FIG. 3 schematically illustrates an expression vector for expressing the tagged peptides.
Figure 4:
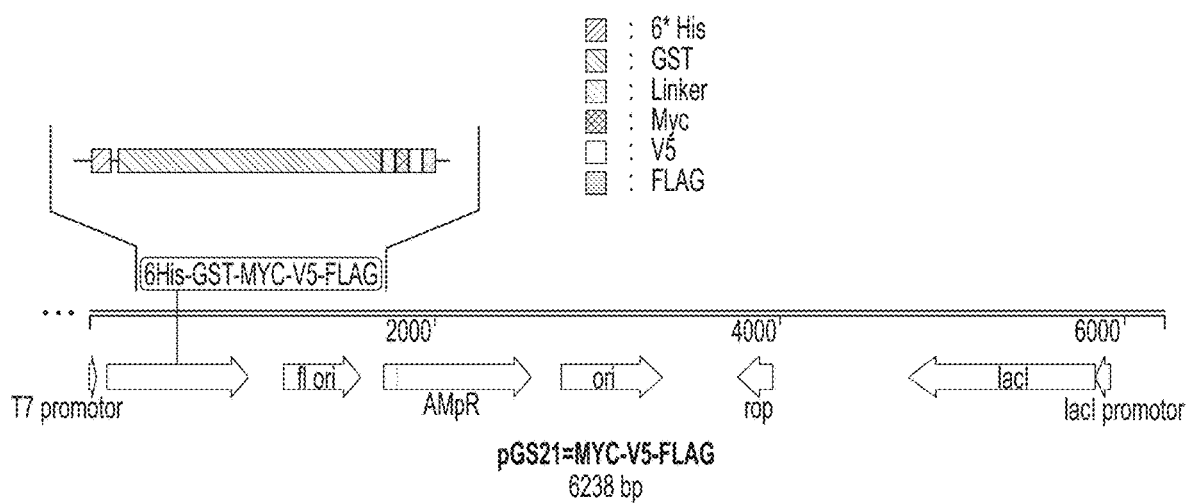
FIG. 4 schematically illustrates the tagged peptide array.

According to embodiments illustrated in FIG. 3, an expression vector of tagged peptides can be constructed to contain optionally one or more affinity tag DNA sequences, a linker DNA sequence, optionally a protease recognition site, a multiple cloning site for inserting peptide expression DNA sequence.

In the above-mentioned embodiments, those skilled in the art will know that the expression vector can be constructed based on, but not limited to, a bacteria expression vector, an yeast expression vector, an insect expression vector, a fungal expression vector, a mammalian expression vector, and a plant expression vector.

In another embodiment of the present invention, the tagged peptides can be expressed in and purified from an expression host. The expression host is selected from the group consisting of, but not limited to, a bacteria cell, an yeast cell, an insect cell, a fungal cell, a mammalian cell, and a plant cell.

It is readily appreciated by those skilled in the art that, similar methods can also be generally applied for constructing a peptide library. The designed peptides are expressed, purified using an affinity tag immobilized on a solid surface, and then used for screening with the peptides still attached to the solid surface. The designed peptides can also be eluted from the solid surface and then used for screening.

Various embodiments of the invention have now been described. It is to be noted, however, that this description of these specific embodiments is merely illustrative of the principles underlying the inventive concept. It is therefore contemplated that various modifications of the disclosed embodiments will, without departing from the spirit and scope of the invention, be apparent to persons skilled in the art.

The following specific examples are further illustrative of the nature of the invention, it needs to be understood that the invention is not limited thereto.

EXAMPLE

Protein Display

The DNA sequence of a three peptide array (Myc-V5-Flag, GAACAGAAACTGATTAGCGAGGAAGACCTT-GGTAAACCGATTCCGAACCCGTTGC TGGGCCTGGACAGCACG-GACTATAAAGATGAC-GATGACAAA (SEQ ID NO: 1)) was cloned into the pGS21 vector after GST gene sequence using the standard cloning method, a linker sequence of TCGGATCTGGGC-CACACAGGCCATA-GATCTGGTACCGACGACGACGACAAGGCCA TGGGT (SEQ ID NO: 2) was also added between GST and the peptide array. The GST-tagged peptide was expressed in an *E. coli* strain using IPTG as the inducer.

The GST-tagged peptide was purified using a Ni-IDA column. The GST-tagged peptide was bound onto the Ni-NDA column and eluted from the column with 300 mM Imidazole. The elution was dialyzed against a dialysis solution (0.01 M Tris-HCl, pH 7.6, in water).

Figure 5:
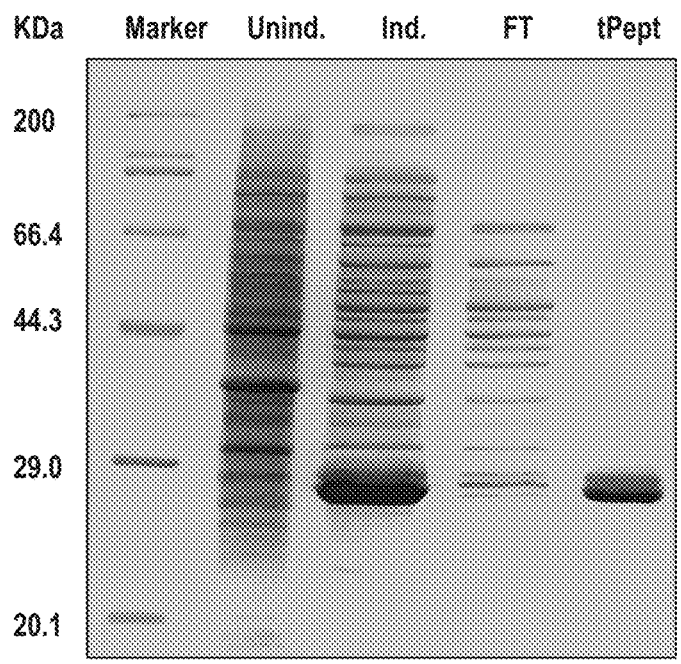
FIG. 5 schematically illustrates the expression and purification of the tagged peptide array.

FIG. 5 shows that the GST-tagged peptide array was expressed an a soluble protein, wherein the Lane Marker is a protein marker with the molecular weight listed on the left, Lane 1 is the whole proteins without induction (Unind.), Lane 2 is the whole proteins with 1 mM IPTG induction (Ind.), Lane 3 is the flowthrough (FT) of the sample, and Lane 4 is the purified GST-tagged peptide (tPept.).

Figure 6:
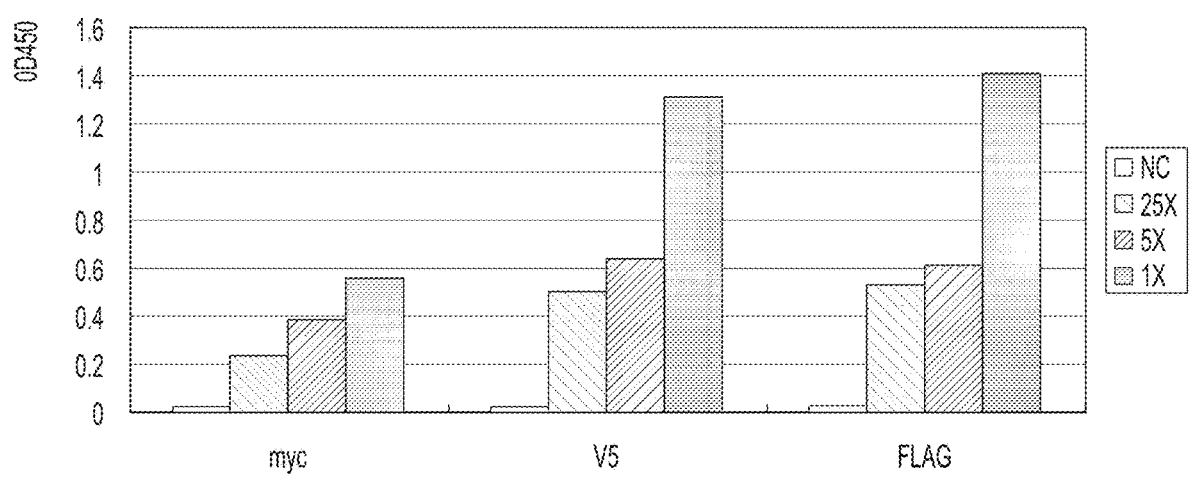
FIG. 6 schematically illustrates the detection and analysis of the tagged peptide array.

FIG. 6 illustrates the ELISA results. The assay was performed using the standard ELISA method with HRP-labeled secondary antibody. Each of the three peptides (Myc-V5-Flag with amino acid sequence of EQKLISEEDL-GKPIPNPLLGLDST-DYKDDDDK (SEQ ID NO: 3)) can be recognized and detected by the corresponding antibody. NC is a negative control. 1X means that the purified sample was not diluted and used directly for ELISA assay, while 5X and 25X mean that the purified sample was diluted 5 times and 25 times, respectively. TMB solution was used as the substrate for HRP.

All publications and patents referred to herein are incorporated by reference. Various modifications and variations of the described subject matter will be apparent to those skilled in the art without departing from the scope and spirit of the invention. Although the invention has been described in connection with specific embodiments, it should be understood that the invention as claimed should not be unduly limited to these embodiments. Indeed, various modifications for carrying out the invention are obvious to those skilled in the art and are intended to be within the scope of the following claims.

The invention claimed is:

1. A method of constructing a peptide library including a complete tetrapeptide library containing all 160,000 possible tetrapeptide sequences, the method comprising constructing the complete tetrapeptide library, wherein constructing the complete tetrapeptide library comprises:
   (i) designing 3405 tagged peptides, each comprising an affinity tag, so that each of the 3405 tagged peptides contains an array of distinct and overlapping tetrapeptide sequences, wherein each of the 3405 tagged peptides comprises an array of 50 amino acids containing no more than 47 distinct and overlapping consecutive tetrapeptide sequences, wherein each of the 47 distinct and overlapping consecutive tetrapeptide sequences in each of the 3405 tagged peptides is a distinct tetrapeptide sequence of the 160,000 possible tetrapeptide sequences, and wherein all 160,000 possible tetrapeptide sequences are contained in the 3405 tagged peptides;
   (ii) constructing a series of expression vectors with each vector expressing a single tagged peptide, and producing the 3405 tagged peptides by expressing the single tagged peptide from each vector;
   (iii) purifying the 3405 tagged peptides by binding the affinity tag to an immobilized solid surface; and
   (iv) eluting the 3405 tagged peptides and using the complete peptide tetrapeptide library for screening, or
   (v) using the immobilized peptides directly for screening without being eluted from the solid surface.

2. The method of claim 1, wherein the tag is selected from the group consisting of GST, Trx, SUMO, CBD, FLAG, HA, AviTag, His Tag, Myc-Tag, SBP, Strep-Tag, Fc-Tag, Halo-Tag, V5, VSV, and MBP.

3. The method of claim 1, wherein said expressing is performed in an expression host selected from the group consisting of a bacteria cell, a yeast cell, an insect cell, a fungal cell, a mammalian cell, and a plant cell.

4. The method of claim 1, wherein the expression vector is selected from the group consisting of a bacteria expression vector, a yeast expression vector, an insect expression vector, a fungal expression vector, a mammalian expression vector, and a plant expression vector.

5. The method of claim 1, wherein a peptide sequence of a linker is present between the tag and the array of 50 amino acids to increase the accessibility of the array of 50 amino acids.

6. The method of claim 1, wherein a protease recognition sequence is present between the tag and the array of 50 amino acids so that the array of 50 amino acids can be cleaved from the tag using a protease.

7. A method of constructing a peptide library including a complete pentapeptide library containing all 3,200,000 possible pentapeptide sequences, the method comprising constructing the complete pentapeptide library, wherein constructing the complete pentapeptide library comprises:
   designing 69,566 tagged peptides, each comprising an affinity tag, so that each of the 69,566 tagged peptides contains an array of distinct and overlapping pentapeptide sequences, wherein each of the 69,566 tagged peptides comprises an array of 50 amino acids containing no more than 46 distinct and overlapping consecutive pentapeptide sequences, wherein each of the 46 distinct and overlapping consecutive pentapeptide sequences in each of the 69,566 tagged peptides is a distinct pentapeptide sequence of the 3,200,000 possible pentapeptide sequences, and wherein all 3,200,000 possible tetrapeptide sequences are contained in the 69,566 tagged peptides;
   cloning the 69,566 tagged peptides into expression vectors;
   expressing the 69,566 tagged peptides; and
   purifying the 69,566 tagged peptides to constitute the complete pentapeptide library.

8. The method of claim 7, wherein the tag is selected from the group consisting of GST, Trx, SUMO, CBD, FLAG, HA, AviTag, His Tag, Myc-Tag, SBP, Strep-Tag, Fc-Tag, Halo-Tag, V5, VSV and MBP.

9. The method of claim 7, wherein the 69,566 tagged peptides are GST-tagged 50-mer peptides.

\* \* \* \* \*

SEQUENCE LISTING

<160> NUMBER OF SEQ ID NOS: 3

<210> SEQ ID NO 1
<211> LENGTH: 96
<212> TYPE: DNA
<213> ORGANISM: Artificial Sequence
<220> FEATURE:
<223> OTHER INFORMATION: Myc-V5-Flag

<400> SEQUENCE: 1

```
gaacagaaac tgattagcga ggaagacctt ggtaaaccga ttccgaaccc gttgctgggc    60
ctggacagca cggactataa agatgacgat gacaaa                              96
```

<210> SEQ ID NO 2
<211> LENGTH: 60
<212> TYPE: DNA
<213> ORGANISM: Artificial Sequence
<220> FEATURE:
<223> OTHER INFORMATION: linker sequence

<400> SEQUENCE: 2

```
tcggatctgg gccacacagg ccatagatct ggtaccgacg acgacgacaa ggccatgggt    60
```

```
<210> SEQ ID NO 3
<211> LENGTH: 32
<212> TYPE: PRT
<213> ORGANISM: Artificial Sequence
<220> FEATURE:
<223> OTHER INFORMATION: Myc-V5-Flag

<400> SEQUENCE: 3

Glu Gln Lys Leu Ile Ser Glu Glu Asp Leu Gly Lys Pro Ile Pro Asn
1               5                   10                  15

Pro Leu Leu Gly Leu Asp Ser Thr Asp Tyr Lys Asp Asp Asp Asp Lys
            20                  25                  30
```